United States Patent [19]

Dahmer et al.

[11] Patent Number: 5,731,458
[45] Date of Patent: Mar. 24, 1998

[54] PROCESS FOR THERMALLY CRACKING CARBAMIC ACID ESTERS

[75] Inventors: Jürgen Dahmer, Köln; Dieter Schleenstein, Odenthal; Heinrich Steude, Leverkusen; Oswald Wilmes, Köln; Christian Rasp, Gladbach; Georg Ronge; Klaus Nachtkamp, both of Düsseldorf; Wilfried Litz, Köln; Stephan Kabelac, Wunstdorf, all of Germany

[73] Assignee: Bayer Aktiengesellschaft, Leverkusen, Germany

[21] Appl. No.: 811,801

[22] Filed: Mar. 6, 1997

[30] Foreign Application Priority Data

Mar. 15, 1996 [DE] Germany ............ 196 10 261.8
May 10, 1996 [DE] Germany ............ 196 18 828.8

[51] Int. Cl.$^6$ .................................................. C07C 263/04
[52] U.S. Cl. ................................................... 560/345
[58] Field of Search ....................................... 560/345

[56] References Cited

U.S. PATENT DOCUMENTS

| | | | |
|---|---|---|---|
| 3,734,941 | 5/1973 | Sydor | 260/453 P |
| 3,870,739 | 3/1975 | DeLaMater et al. | 260/453 P |
| 4,330,479 | 5/1982 | Merger et al. | 260/453 P |
| 4,482,499 | 11/1984 | Merger et al. | 260/453 P |
| 4,530,796 | 7/1985 | Mattner et al. | |
| 4,596,678 | 6/1986 | Merger et al. | 560/344 CM |
| 4,596,679 | 6/1986 | Hellbach et al. | 560/344 |
| 4,599,401 | 7/1986 | Koleske | 528/408 |
| 4,613,466 | 9/1986 | Merger et al. | 560/344 |
| 4,692,550 | 9/1987 | Engbert et al. | 560/345 |
| 4,748,226 | 5/1988 | Merger et al. | 528/85 |
| 5,284,969 | 2/1994 | Hauner et al. | 560/345 |
| 5,360,931 | 11/1994 | Bohmholdt et al. | 560/344 |
| 5,554,787 | 9/1996 | Merger et al. | 560/355 |

FOREIGN PATENT DOCUMENTS 524554  1/1993  European Pat. Off. .

*Primary Examiner*—Samuel Barts
*Attorney, Agent, or Firm*—Joseph C. Gil; Thomas W. Roy

[57] ABSTRACT

This present invention relates to a process for thermally cracking carbamic acid esters into the corresponding isocyanate and hydroxyl compounds in the liquid phase, wherein the reaction proceeds as a reactive rectification in the stripping zone of a column and in an inert, high-boiling solvent, which acts as a buffer to keep the reaction away from the evaporator region of the column.

7 Claims, No Drawings

PROCESS FOR THERMALLY CRACKING CARBAMIC ACID ESTERS

BACKGROUND OF THE INVENTION

1. Field of the Invention

This present invention relates to a process for thermally cracking carbamic acid esters into the corresponding isocyanates and hydroxyl components in the liquid phase, wherein the reaction proceeds as a reactive rectification in the stripping zone of a column and an inert, high-boiling solvent acts as a buffer and keeps the reaction away from the evaporator region of the column.

2. Description of the Prior Art

It is known that the cracking of carbamic acid esters to form isocyanates can be conducted in the gaseous or liquid phases or in a fluidized bed, e.g., as described in EP-A-28, 724, EP-A 100,047, EP-A 126,299, EP-A 126,300, EP-A 143,120, EP-A261,604, EP-A 449,110, U.S. Pat. No. 3,734, 941 and U.S. Pat. No. 3,870,739.

Cracking in the gas phase is a high-temperature process, and is generally conducted at temperatures of >300° C. in a vacuum of <25 mbar. Due to the cost of the process technology, the thermal loading of the starting materials and products and the need gasify the carbamic acid ester, as well as the catalytic effects of metal surfaces, which are still in part unexplained, cracking in the gas phase is disadvantageous compared to cracking in the liquid phase. In particular, there is a risk of blockages in the evaporator region due to encrustations, since the problem of removing high molecular weight secondary products has not been solved.

Cracking in a fluidized bed is described, e.g., in EP-A 78,005. This process is burdened with high energy usage and difficulties are anticipated for its industrial implementation, so that its use on an industrial scale is not presently foreseeable due to the need for further development work.

Compared with gas phase cracking, cracking in the liquid phase may be carried out at lower reaction temperatures of <300° C., but necessitates rapid separation of the reaction products. This is necessary for two reasons: 1) to prevent the isocyanate and hydroxyl components from again reacting to form carbamic acid esters, i.e., rereacting, and 2) to reduce or prevent the formation of resin-like by-products which can result in deposits in the apparatus used. Reduction of the reaction temperature is achieved by the addition of catalysts. The formation of high molecular weight secondary products can be reduced by dilution with an inert solvent. The solvent also serves to remove these by-products from the system. The disadvantageous effects of the catalysts are the enhanced occurrence of secondary reactions and the potential contamination of the product. The processes listed below can be distinguished by the type of reactor they are conducted in, e.g., in a stirred reactor or thin-film reactor, in a reactor with a fitted column, and in reaction columns. A further distinguishing feature is the presence or absence of a solvent during the cracking reaction.

A solvent-free cracking reaction which employs a catalyst is known for a reactor with a fitted column from EP-A 524,554. The specially fashioned reactor which forms the basis of this process enables cracking to be conducted in a two-phase mixture with a volumetric gas content of >50%. Separation without appreciable rereaction, like that which is achieved using reflux condensers, is achieved here by rectification. The disadvantages to be expected with this reactor are a large overall volume and the risk of dry heating surface regions being occupied, particularly if there are departures from the rated loading situation. The reaction takes place directly in the region of the heating surfaces here, where severe temperature gradients and poorly defined dwell times exist.

A cracking column is also described in EP-A 542,106, which relates to cracking without a catalyst and in the presence of a high boiling solvent in a distillation column which serves as a cracking reactor. The cracked products are separated from each other by reflux condensers, and the carbamic acid ester is fed into the bottom zone of the column. The separation between the alcohol and the crude isocyanate is unsatisfactory.

In addition, the majority of the cracking in the process described according to EP-A 542,106 takes place in the bottom of the column. Even though the bottom of the column provides favorable conditions for complete reaction due to its elevated temperature level compared with the distillation column and due to its high dwell time, it is not possible to carry out cracking to completion with this process. The reaction between the by-products in the bottom of the column can lead to caked deposits and losses in yield, and subsequent work-up is difficult. It is known that caked deposits which are formed from secondary products can severely shorten the service life of the apparatus.

In principle, the known processes for cracking of carbamic acid esters in the liquid phase are advantageous compared with gas phase processes, since in the liquid phase the high thermal loading of the reaction products is reduced. When cracking is conducted in the liquid phase without solvent, the careful supply of energy for the strongly endothermic cracking process and the rapid removal of thermally sensitive cracking products from the "hot" zone is very difficult. One disadvantage of the aforementioned processes is that the cracking reaction is predominantly carried out in a heated reactor or in the evaporator region of the cracking column. Deposits are formed primarily on the heated surfaces, particularly when no solvent is used. A further disadvantage of processes without solvents is the high rates of outward transfer which are necessary to reduce the dwell time in the column bottom and for the discharge of the by-products.

An object of the present invention is to provide a process for the continuous cracking of carbamic acid esters with an inert solvent and with the simultaneous, continuous, rapid separation of the cracking products from the starting material and with separation of the cracking products from each other (reactive rectification). The process had to be capable of being operated economically on an industrial scale with a high space-time yield, without its operation being significantly impeded by the formation of polymeric deposits.

This object has been achieved according to the invention by conducting the cracking reaction in the form of a reactive rectification in the stripping zone of a column, wherein the reaction products are rapidly and effectively separated from the starting material by the counter-current principle. The reaction is prevented from proceeding in the evaporator region by the presence of a suitable high boiling solvent, wherein the solvent transfers heat energy from the evaporator into the reaction or stripping zone by evaporation and condensation. One of the two product streams is taken off as a side stream, wherein an optimum profile can be achieved by the reflux separator.

It has surprisingly been found that the cracking of carbamic acid esters can be conducted directly, with a high space-time yield, in a rectifier column in such a way that no carbamic acid ester comes into contact with the heating surfaces in the evaporator such that the apparatus can thus operate for long periods of time. In contrast to the column described in DE-A 4,231,417, and in contrast also to the reactor described in EP-A 0,524,554, only a low rate of removal of the bottom contents is necessary, since neither carbamic acid esters nor cracking products nor by-products can be detected analytically at this location. In contrast to DE-A 4,231,417, the dwell time of the boiling liquid in the reaction zone is not as short as possible, but is matched to the kinetics of cracking.

SUMMARY OF THE INVENTION

The present invention relates to a process for thermally cracking a carbamic acid ester to form an isocyanate and a hydroxyl compound by a) introducing a carbamic acid ester, optionally in dissolved form, at a temperature above the melting point of the ester into the inlet of a reactive rectification apparatus containing an evaporator zone, a reaction/stripping zone, a middle zone, an enrichment zone and a top zone containing a liquid separator and a condenser, said column having an inlet in the middle zone, an outlet in the evaporator zone, an outlet in the liquid separator and an outlet between the middle zone and the enrichment zone that is above the inlet, b) thermally cracking the carbamic acid esters at a temperature of 150° C. to 400° C. in the reaction/stripping zone of the column in the presence of a high boiling compound which is a solvent for the carbamic acid esters, is substantially inert to the carbamic acid esters and the products of the decomposition reaction, and carries heat energy from the evaporator into the reaction/stripping zone of the column, c) separating the products of the decomposition reaction into a fraction consisting of at least 95% by weight alcohol and into an isocyanate fraction corresponding to at least 90% by weight of the carbamic acid ester used in the enrichment zone, d) maintaining the solvent above its boiling point in the evaporator zone by maintaining the evaporator zone at a pressure of 2 to 1000 mbar and a temperature of 150° C. to 400° C., e) adjusting the dwell time and the mass and heat transfer in the reaction/stripping zone and middle zone by suitable baffles so that cracking of the carbamic acid ester takes place in these zones, removing the hydroxyl compound from the liquid separator in the top zone and the isocyanate component from the outlet between the middle zone and the enrichment zone and f) removing the hydroxyl compound from the liquid separator in the top zone and the isocyanate component from the outlet between the middle zone and the enrichment zone and g) removing from the outlet in the evaporator zone an amount of the high boiling compound, which may contain impurities, which approximately corresponds to the amount of high boiling compound which is fed into the apparatus.

DETAILED DESCRIPTION OF THE INVENTION

When carrying out the process according to the invention, the isocyanate-rich fraction withdrawn as the side stream can be purified by distillation such that the bottoms of the distillation column, which contain partially cracked carbamic acid esters, may either be completely or partially recycled to the feed to the cracking column and/or may be fed into the urethane synthesis step in a cyclic process.

In the process according to the invention the bottom discharge can also be subjected to distillation. The lower boiling fraction, which is essentially solvent, may be recycled as feed to the cracking column.

Higher rates of discharge are only necessary if the reactor feed already contains higher proportions of by-products and/or if the solvent exhibits a tendency towards the formation of by-products to an increased extent.

In accordance with the process of the present invention it is possible to attain substantially completely cracking of the carbamic acid ester, with minimal by-products, even in the stripping zone. The result of this is that losses in yield are prevented due to the complete cracking, subsequent work-up is considerably simplified because of reduced by-products, and secondary reactions and caked deposits in the bottom are prevented, primarily because the products of the decomposition reaction products do not enter the column bottom to a measurable extent, so that there is a distinct increase in lifetimes of the equipment.

In some cases cracking can proceed significantly better in packed columns, even with a lower hold-up and a reduced dwell time, than in plate columns.

It is essential to the invention that the reaction proceeds as a rectification reaction in the presence of the inert solvent. The condensation of the solvent vapor rising from the evaporator provides energy for the endothermic decomposition reaction and for partial evaporation of the reaction products in the reaction/stripping zone. Because the inert solvent should preferably have a narrow boiling range and a high thermal stability, a pure substance is preferred.

The carbamic acid esters to be used in the process according to the invention are compounds corresponding to the general formula $R^1(NHCOOR^2)_n$, in which $R^1$ is an aliphatic hydrocarbon radical containing a total of from about 4 to 12 carbon atoms and, optionally, bearing inert substituents; a cycloaliphatic hydrocarbon radical containing a total of from about 6 to 15 carbon atoms and, optionally, bearing inert substituents; an araliphatic hydrocarbon radical containing a total of from about 7 to 10 carbon atoms and, optionally, bearing inert substituents; or an aromatic hydrocarbon radical containing a total of from about 6 to 15 carbon atoms and, optionally, inert substituents;

$R^2$ is an aliphatic hydrocarbon radical containing from about 1 to 20 carbon atoms, a cycloaliphatic hydrocarbon radical containing from about 5 to 15 carbon atoms or an aromatic hydrocarbon radical containing from about 6 to 15 carbon atoms and n is an integer of from 2 to 5.

The carbamic acid esters preferably used in the process according to the invention are those corresponding to the above formula in which $R^1$ is an aliphatic hydrocarbon radical containing a total of from 4 to 12 and, more particularly, from 5 to 10 carbon atoms; a cycloaliphatic hydrocarbon radical containing from 6 to 15 carbon atoms; a xylylene radical or an aromatic hydrocarbon radical containing a total of from 6 to 15 carbon atoms and, optionally, bearing methyl substituents and/or methylene bridges;

$R^2$ is an aliphatic hydrocarbon radical containing from 1 to 6 and, more particularly, from 1 to 4 carbon atoms; a cyclohexyl radical; or a phenyl radical; and n is an integer of from 2 to 4.

Particularly preferred carbamic acid esters for the process according to the invention are those corresponding to the general formula

in which

R¹ is the hydrocarbon radical linking the isocyanate groups of 1,6-diisocyanatohexane, 1-isocyanato-3,3,5-trimethyl-5-isocyanatomethyl cyclohexane, 2,4-diisocyanatotoluene, 2,6-diisocyanatotoluene, 2,2'-, 2,4'- or 4,4'-diisocyanatodiphenyl methane, 2,4'- or 4,4'-diisocyanatodicyclohexyl methane or 1,5-diisocyanato-naphthalene and R² is a $C_{1-4}$ alkyl radical.

Examples of suitable carbamic acid esters are
1-(butoxycarbonylamino)-3,3,5-trimethyl-5-(butoxycarbonyl-aminomethyl)-cyclohexane,
1-(methoxycarbonylamino)-3,3,5-trimethyl-5-(methoxycarbonylaminomethyl)-cyclohexane,
1-methyl-2,4-bis-(methoxycarbonylamino)-benzene,
1-methyl-2,6-bis-(methoxycarbonylamino)-benzene,
1-methyl-2,4-bis-(butoxycarbonylamino)-benzene,
1-methyl-2,6-bis-(butoxycarbonylamino)-benzene,
1,10-bis-(methoxycarbonylamino)-decane,
1,12-bis-(butoxycarbonyl amino)-dodecane
1,12-bis-(methoxycarbonylamino)-dodecane,
1,12-bis-(phenoxycarbonylamino)-dodecane,
1,3-bis-(ethoxycarbonylaminoaminomethyl)-benzene,
1,3-bis-(methoxycarbonylamino)-benzene,
1,3-bis-[(methoxycarbonylamino)-methyl]-benzene,
1,3,6-tris-(methoxycarbonylamino)-hexane,
1,3,6-tris-(phenoxycarbonylamino)-hexane,
1,4-bis-(ethoxycarbonylamino)-butane,
1,4-bis-(ethoxycarbonylamino)-cyclohexane,
1,5-bis-(butoxycarbonylamino)-naphthalene,
1,6-bis-(methoxycarbonylamino)-hexane,
1,6-bis-(methoxycarbonylamino)-hexane,
1,6-bis-(butoxycarbonylamino)-hexane,
1,5-bis-(methoxycarbonylamino)-pentane,
1,6-bis-(methoxymethylcarbonylamino)-hexane,
1,8-bis-(ethoxycarbonylamino)-octane,
1,8-bis-(phenoxycarbonylamino)-4-(phenoxycarbonylaminomethyl)-octane,
2,2'-bis-(4-propoxycarbonylaminophenyl)-propane,
2,4'-bis-(ethoxycarbonylamino)-diphenyl methane,
2,4-bis-(methoxycarbonylamino)-cyclohexane,
4,4'-bis-(ethoxycarbonylamino)-dicyclohexane methane,
2,4'-bis-(ethoxycarbonylamino)-diphenyl methane,
4,4'-bis-(methoxycarbonylamino)-2,2'-dicyclohexyl propane,
4,4'-bis-(methoxycarbonylamino)-biphenyl,
4,4'-bis-(butoxycarbonylamino)-2,2'-dicyclohexyl propane,
4,4'-bis-(phenoxycarbonylamino)-dicyclohexyl methane and
4,4'-bis-(phenoxycarbonylamino)-diphenyl methane The butoxy groups" mentioned are iso- and n-butoxy groups. Suitable solvents include dibenzyl toluenes, partially hydrogenated terphenyls, phenoxybiphenyls and mixtures thereof.

The cracking products rise in vapor form and are thus directly removed from the liquid phase reaction. During the cracking of multi-functional carbamic acid esters, the partially cracked intermediate product may be deposited in the region between the feed and the side take-off and can be recycled into the reaction zone for complete cracking. The separation between the hydroxyl and isocyanate components occurs in the enrichment zone of the column, which is above the side take-off. Any hold up of the liquid should be as short as possible to prevent rereaction of the cracked components.

According to the invention, the enrichment zone and the middle zone of the column can be operated at a pressure which is reduced by up to 900 mbar when compared with the reaction/stripping zone of the column. The amount of the pressure difference depends upon the pressure in the bottom zone of the column. The difference in pressure may be attained by placing the enrichment and middle zones in a separate apparatus to segregate these zones from the other zones of the column.

In addition, the possibility of the decomposition products rereacting to form carbamic acid esters can be lessened by reducing the pressure in the enrichment zone only, which results in a reduced temperature and, thus, in a slower rereaction.

Rectifier columns in which the reaction/stripping zone has a sufficiently long dwell time and the enrichment zone has a shorter dwell time are suitable as the apparatus. The dwell time in the stripping zone has to be matched to the kinetics and mass transfer of cracking and is therefore strongly dependent on the substances present. The dwell time ranges from 1 to 1000 minutes, preferably 5 to 200 minutes, and is defined as the ratio of the liquid hold-up in the stripping zone to the volume flow of the liquid phase feed. Packings with a low pressure drop and with a high hold-up are preferred in this regard, preferably in combination with a solvent having a narrow boiling range. In this way it is possible to achieve a temperature which is approximately constant over the reaction zone of the column and which is freely selectable by the absolute pressure employed. The temperature in the reaction zone should preferably be selected such that the 1) the reaction proceeds sufficiently rapidly and 2) the formation of by-products which cannot be recycled does not occur at all or occurs only to a slight extent.

The column has a reflux at the top, at least one side take-off for the partial or complete removal of the liquid phase, and a bottom outlet.

All common evaporators are suitable as evaporators for the column. For lasting operation, the heating surfaces must be well wetted and flushed all round. Bubble cap bases, sieve plates or ordered or random packings are possible as baffles in the middle part, stripping zone and enrichment zone of the column. Ordered packings are preferred.

As in the processes according to EP-A 54,817, EP-A 92,738 and EP-A 355,443, the cracking products can also be separated by reflux condensers, but they are preferably separated according to the present invention by rectification.

The reactor feed consists of the carbamic acid ester and optionally a catalyst, an inert solvent and/or recycled by-products. The carbamic acid ester is produced from an amine, a carbonyl source (such as oxides of carbon or carboxylic acid derivatives, preferably urea, carbamic acid esters or dialkyl carbonates) and a hydroxyl component. All or a portion of the recycled solvent may optionally be introduced directly into the bottom of the column.

The feed stream to the cracking column is primarily composed of a stream from the carbamic acid formation process and optionally a) a stream which contains recovered and is low in by-products, which is obtained by separating high boiling by-products from the discharge from the bottom of the cracking column, optionally b) the bottom discharge, which contains partially cracked carbamic acid esters, from the bottom isocyanate purification column, optionally c) fresh solvent, and optionally d) the top product from the purification column. The feed is preheated to a temperature which is up to 250° C. above the melting temperature of the carbamic acid ester but which is preferably 50° C. below the reaction temperature. The feed is introduced into the column above the stripping part.

In order to increase the reaction rate, cracking of the carbamic acid esters can be conducted in the presence of catalysts; however, they are normally not necessary. If catalysts are added, they are preferably used in amounts of up to 10% by weight, preferably up to 3% by weight, based on the weight of the carbamic acid ester. Examples of suitable catalysts include metals, metal oxides, inorganic or organic metal compounds, and acidic additives. For example, those disclosed in U.S. Pat. No. 3,919,279, U.S. Pat. No. 4,388,246, DE-A 3,277,748, DE-A 3,248,018, DE-A 3,314,790, U.S. Pat. No. 4,873,365, EP-A 323,514, EP-A 126,299, EP-A 566,925 and EP-A 568,782. The process may also be catalyzed heterogeneously by the use of packing material or tower packing surfaces which have a suitable action.

The cracking column is operated at a bottom pressure of 2 to 1000 mbar, preferably 20 to 200 mbar. The bottom temperature is 150 to 400° C., preferably 220 to 300° C. The bottom temperature primarily depends upon the boiling temperature of the solvent, and should be selected such that secondary reactions of the carbamic acid ester only occur to a slight extent. The reflux ratio at the column top is between 0.2 and 20, preferably 2 to 10. The reflux ratio at the side stream take-off is between 0 and 40, preferably between 5 and 20.

The bottom discharge serves to remove by-products of the solvent, which may not be completely inert, from the system, and also serves to remove high boiling impurities which are present in the feed stream with the carbamic acid ester. The amount of solvent to be fed in or discharged only needs to be that which is necessary to maintain a predetermined by-product concentration in the column bottom. In contrast to the processes of EP-A 0,524,554 and DE-A 4,231,417, complete cracking of the carbamic acid ester normally occurs in the first pass through the column, so that generally no starting material has to be recycled. High boiling impurities can be transferred out of the bottom take-off stream in a downstream apparatus in known manner, e.g., by vacuum distillation, by thin-film distillation and/or by falling film distillation. The solvent-rich stream recycled to the cracking column. The isocyanate-rich side stream from the cracking column is subsequently subjected to a purification distillation step.

The bottoms from the purification distillation step are normally admixed with the feed to the cracking column; if the amount of high molecular weight by-products is higher, the bottoms may also be completely or partially recycled to the urethane production stage or may be discarded.

EXAMPLE 0.91 kg/hour of a mixture of hexamethylene-di-n-butylurethane-1,6 (HDU-B) was continuously fed into a cracking column together with 0.3 kg/hour of ortho-phenoxybiphenyl (content >99% by GC). The HDU-B and ortho-phenoxybiphenyl were fed in above the stripping zone of the column.

The column consisted of an evaporator with 4 horizontally disposed heater plug inserts. Above the evaporator is the stripping zone, which has an overall length of 8.1 m and contains an ordered packing having a diameter of 70 mm and a liquid hold-up of about 1500 ml. The feed inlet was situated above this reaction zone; the HDU-B was metered in at 120° C. and the solvent was metered in at 160° C. The middle zone of the column had a diameter of 70 mm and an effective height of 990 mm, and was filled with cloth packing pieces over an effective height of 990 mm. Above this was the side stream take-off, followed by the enrichment zone having an effective length of cloth packing having a diameter of 50 mm. The top of the column contained a liquid separator and a water-cooled condenser. The column was insulated. In this example the top reflux ratio was 7, and the side stream reflux ratio was 10. The top pressure was 85 mbar and the bottom temperature was 260° C.

0.3 kg/hour of liquid were taken off from the column bottom. When analyzed by supercritical fluid chromatography (SFC), this liquid only contained the heat transfer medium. HDU-B or its secondary products were not detected (detection limit 0.1%). The same result was obtained by IR analysis. The liquid which drained off into the bottom from the stripping zone was also sampled and found to be just as pure. Here also, no impurities were found either by SFC or by IR analysis.

The side stream of 0.48 kg/hour contained of 98.2% by weight of HDI, 1.6% by weight of a semi-cracked product corresponding to formula (I)

0.1% by weight of ortho-phenoxybiphenyl and 0.1% by weight of BuOH. The top take-off stream of 0.43 kg/hour had a composition of 99.5% BuOH, 0.2% by weight HDU-B and 0.3% by weight of (I). The yield (maximum possible amount of HDI less the losses in the column bottom and top) in this test was considerably greater than 99%. In this respect, the content of (I) in the side stream was not assessed as a loss, since (I) can be recovered via the reflux from the purification column. The yield can be further increased if the top product is recycled.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for thermally cracking a carbamic acid ester to form an isocyanate and a hydroxyl compound which comprises a) introducing a carbamic acid ester, optionally in dissolved form, at a temperature above the melting point of the ester into the inlet of a reactive rectification apparatus containing an evaporator zone, a reaction/stripping zone, a middle zone, an enrichment zone and a top zone containing a liquid separator and a condenser, said column having an inlet in the middle zone, an outlet in the evaporator zone, an outlet in the liquid separator and an outlet between the middle zone and the enrichment zone that is above the inlet, b) thermally cracking the carbamic acid esters at a temperature of 150° C. to 400° C. in the reaction/stripping zone of the column in the presence of a high boiling compound which is a solvent for the carbamic acid esters, is substantially inert to the carbamic acid esters and the products of the decomposition reaction, and carries heat energy from the evaporator into the reaction/stripping zone of the column, c) separating the products of the decomposition reaction into a fraction consisting of at least 95% by weight alcohol and into an isocyanate fraction corresponding to at least 90% by weight of the carbamic acid ester used in the enrichment zone, d) maintaining the solvent above its boiling point in the evaporator zone by maintaining the evaporator zone at a pressure of 2 to 1000 mbar and a temperature of 150° C. to 400° C., e) adjusting the dwell time and the mass and heat transfer in the reaction/stripping zone and middle zone by suitable baffles so that cracking of the carbamic acid ester takes place in these zones, f) removing the hydroxyl compound from the liquid separator in the top zone and the isocyanate component from the outlet between the middle zone and the enrichment zone and g) removing from the outlet in the evaporator zone an amount of the high boiling compound, which may contain impurities, which approximately corresponds to the amount of high boiling compound which is fed into the apparatus.

2. The process of claim 1 which comprises distilling the isocyanate component to recover a purified isocyanate compound and a bottom fraction and optionally completely or partially recycling the bottom fraction to the inlet to the rectification apparatus.

3. The process of claim 1 which comprises distilling the discharge from the outlet in the evaporator zone and completely or partially recycling the low boiling fraction, which essentially contains the high boiling compound solvent, to the inlet to the rectification apparatus.

4. The process of claim 1 wherein the high boiling compound comprises a member selected from the group consisting of isomeric dibenzyl toluenes, partially hydrogenated terphenyls and phenoxybiphenyls.

5. The process of claim 1 which comprises operating the enrichment zone and optionally the middle zone of the rectification apparatus at a pressure which is reduced compared with the pressure in the reaction/stripping zone.

6. The process of claim 5 which comprises placing the enrichment zone and optionally the middle zone of the rectification apparatus in a separate apparatus.

7. The process of claim 1 which comprises conducting the reaction in the presence of a catalyst.

* * * * *